United States Patent [19]

von Sprecher et al.

[11] Patent Number: 4,863,938

[45] Date of Patent: Sep. 5, 1989

[54] PYRIDINE DERIVATIVES AND THEIR USE AS NOOTROPIC AGENTS

[75] Inventors: Georg von Sprecher, Allschwil; Peter Waldmeier, Ettingen, both of Switzerland

[73] Assignee: Ciba-Geigy Corporation, Ardsley, N.Y.

[21] Appl. No.: 266,311

[22] Filed: Oct. 31, 1988

Related U.S. Application Data

[63] Continuation of Ser. No. 95,798, Sep. 11, 1987, abandoned, which is a continuation-in-part of Ser. No. 25,295, Mar. 12, 1987, abandoned.

[30] Foreign Application Priority Data

Mar. 17, 1986 [CH] Switzerland .................. 1084/86
Jun. 4, 1986 [CH] Switzerland .................. 2269/86

[51] Int. Cl.$^4$ .................. A61K 31/44; A61K 31/40; A61K 31/415; C07D 213/64

[52] U.S. Cl. .................. 514/349; 514/241; 514/242; 514/245; 514/252; 514/269; 514/335; 514/336; 514/340; 514/341; 514/342; 514/343; 514/344; 514/347; 514/348; 546/256; 546/261; 546/277; 546/278; 546/279; 546/280; 546/281; 546/283; 546/284; 546/286; 546/287; 546/288; 546/292; 546/294; 546/295; 546/296; 546/297; 544/215; 544/238; 544/333; 544/405

[58] Field of Search .................. 546/286, 261, 297, 287, 546/288, 294, 295, 296; 514/335, 344, 347, 348, 349

[56] References Cited

U.S. PATENT DOCUMENTS

| | | | |
|---|---|---|---|
| 3,073,851 | 1/1963 | Steiger | 260/397.6 |
| 3,133,078 | 5/1964 | Steiger | 260/307 |
| 3,182,053 | 5/1965 | Steiger | 260/156 |
| 3,184,482 | 5/1965 | Steiger | 260/378 |
| 3,657,214 | 4/1972 | Berrie et al. | 546/296 |
| 4,186,264 | 1/1980 | Pearose et al. | 424/270 |

FOREIGN PATENT DOCUMENTS 1262307 4/1961 France .................. 546/296

OTHER PUBLICATIONS

Chem. Pharma. Bull., vol. 25, No. 11, pp. 2838–2843 (1977).
CA 99:122348j Stanovnik et al., (1983) p. 642.
J. Heterocyclic Chem., vol. 15, pp. 1105–1112 (10/78).
Synthesis, pp. 288–291 (1986).
Khim Geterosikl. Soedin, No. 11, pp. 1549–1554 (1978).
Khim Geterosikl Soedin, No. 12, pp. 1671–1676 (1978).

Primary Examiner—Mary C. Lee
Assistant Examiner—J. Richter
Attorney, Agent, or Firm—JoAnn Villamizar

[57] ABSTRACT

Pyridine derivatives of the formula

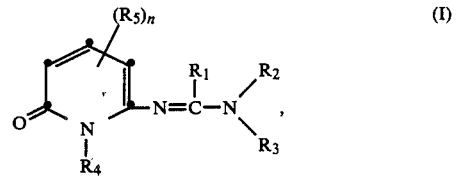

their tautomers and their salts, in which $R_1$, $R_2$, $R_3$, $R_4$, $R_5$ and n have the meanings given in the claims, can be used as active ingredients in medicaments and are manufactured in a manner known per se.

25 Claims, No Drawings

PYRIDINE DERIVATIVES AND THEIR USE AS NOOTROPIC AGENTS

This application is a continuation of application Ser. No. 095,798, filed Sept. 11, 1987, abandoned, which is a continuation-in-part of Ser. No. 025,295, filed Mar. 12, 1987, and now abandoned.

The invention relates to pyridine derivatives of the formula

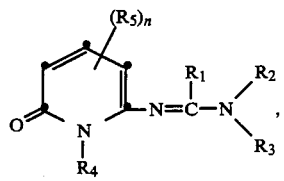

to their tautomers and to their salts, in which $R_1$ represents hydrogen or $C_1$–$C_7$-alkyl, one of the radicals $R_2$ and $R_3$ represents hydrogen, $C_1$–$C_7$-alkyl, aryl-$C_1$–$C_7$-alkyl, $C_3$–$C_6$-alkenyl or $C_3$–$C_6$-alkynyl and the other represents $C_1$–$C_7$-alkyl, aryl-$C_1$–$C_7$-alkyl, $C_3$–$C_6$-alkenyl or $C_3$–$C_6$-alkynyl, $R_4$ represents hydrogen, $C_1$–$C_7$-alkyl or aryl-$C_1$–$C_7$-alkyl and $R_5$ represents $C_1$–$C_7$-alkyl, halogen, $C_1$–$C_7$-alkoxy, $C_1$–$C_7$-alkylthio, $C_1$–$C_7$-alkanesulphinyl, $C_1$–$C_7$-alkanesulphonyl, carboxy, $C_2$–$C_8$-alkoxycarbonyl, carbamoyl, $C_1$–$C_7$-alkylcarbamoyl, di-$C_1$–$C_7$-alkylcarbamoyl, cyano or trifluoromethyl, and the index n represents 0, 1 or 2, and to their manufacture and use, to pharmaceutical preparations containing a compound of the formula I, or a tautomer or salt thereof, and to their manufacture.

Aryl represents especially carbocyclic aryl, for example, unsubstituted or substituted mono- or bicyclic carbocyclic aryl having from 6 up to and including 10 carbon atoms, for example, corresponding phenyl, naphthyl, furthermore indenyl, pentalenyl and azulenyl radicals.

Aryl furthermore represents heterocyclic aryl, for example, unsubstituted or substituted mono cyclic heteroaryl, but can also be a corresponding bicyclic radical, containing up to and including three identical or different hetero atoms, for example, especially selected from the group consisting of nitrogen, oxygen and sulphur. Preferably, corresponding heterocyclic aryl radicals are monocyclic and five- or six-membered and may contain one, two or three nitrogen atoms, an oxygen or sulphur atom, or one or two nitrogen atoms together with an oxygen or sulphur atom. They are, customarily, bonded via a ring carbon atom to the carbon atom in the 4-position of the 1,4-dihydropyridine ring. Corresponding five- and six-membered heteroaryl radicals are, for example, pyrryl, pyrazolyl, imidazolyl, triazolyl, furyl, thienyl, isoxazolyl, oxazolyl, oxadiazolyl, isathiazolyl, thiazolyl, thiadiazolyl, pyridyl, pyridazinyl, pyrimidinyl, pyrazinyl or triazinyl radicals.

The carboxylic and heterocyclic aryl radicals may be substituted, especially mono-, bi-substituted or tri-substituted by the same or different substituents, selected from the group consisting of, for example, halogen, $C_1$–$C_7$-alkyl, $C_1$–$C_7$-alkoxy, hydroxy and $C_1$–$C_8$-alkanoyloxy.

Aryl represents more especially phenyl or naphthyl each of which may be unsubstituted or mono-substituted, or furthermore di- or tri-substituted, for example, by halogen, $C_1$–$C_7$-alkyl, $C_1$–$C_7$-alkoxy, hydroxy and/or by $C_2$–$C_8$-alkanoyloxy. Naphthyl is, for example, 1- or 2-naphthyl. Preferred aryl-$C_1$–$C_7$-alkyl is, for example, phenyl-$C_1$–$C_4$-alkyl, especially benzyl or 2-phenylethyl.

The compounds of the formula I and their salts may be in dynamic equilibrium with corresponding tautomeric forms. The 2-oxo-dihydro-pyridines of the formula I may, for example, if $R_4$ represents hydrogen or if each of $R_3$ and $R_4$ represents hydrogen, be in the form of 2-hydroxy-pyridines of the formula

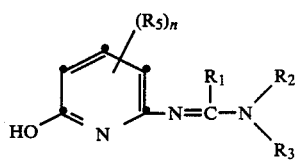

or

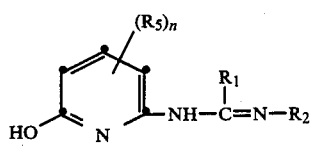

respectively. Likewise, the compounds of the formula I may, if $R_3$ represents hydrogen, be in equilibrium with tautomers of the formula

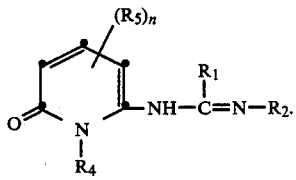

Hereinbefore and hereinafter, the expression "tautomers of the formula I" also includes corresponding compounds of the formulae Ia, Ib and Ic.

If the index n represents 2, $R_5$ may have the same or different meanings. If n is other than 0, $R_5$ preferably represents $C_1$–$C_7$-alkyl, halogen or trifluoromethyl.

Compounds of the formula I may be in the form of acid addition salts, especially pharmaceutically acceptable acid addition salts These are formed, for example, with strong inorganic acids, such as mineral acids, for example sulphuric acid, phosphoric acid or hydrohalic acids, with strong organic carboxylic acids, such as $C_1$–$C_4$-alkanecarboxylic acids, for example acetic acid, such as optionally unsaturated dicarboxylic acids, for example oxalic, malonic, maleic or fumaric acid, or such as hydroxycarboxylic acids, for example tartaric acid or citric acid, or with sulphonic acids, such as $C_1$–$C_4$-alkanesulphonic acid or optionally substituted benzenesulphonic acid, for example methane- or p-toluene-sulphonic acid.

Corresponding acid addition salts may be formed with one or both basic centres and accordingly, for example, pyridinium and/or preferably amidinium salts are obtained.

Also included are salts that are not suitable for pharmaceutical uses, since they can be used, for example, for the isolation or purification of free compounds according to the invention or their pharmaceutically acceptable salts.

Unless defined otherwise, the general definitions used hereinbefore and hereinafter have especially the following meanings.

$C_1$–$C_7$-alkyl is, for example, methyl, ethyl, propyl, isopropyl, n-butyl, isobutyl, sec.-butyl or tert.-butyl and also includes corresponding pentyl, hexyl and heptyl radicals $C_1$–$C_4$-alkyl is preferred.

Halogen is especially halogen having an atomic number of up to and including 35, such as fluorine, chlorine or bromine, also iodine.

$C_1$–$C_7$-alkoxy is, for example, methoxy, ethoxy, propoxy, isopropoxy, n-butoxy, isobutoxy or tert.-butoxy. $C_1$–$C_4$-alkoxy is preferred.

$C_1$–$C_7$-alkylthio is, for example, methyl-, ethyl-, propyl-, isopropyl-, n-butyl-, sec.-butyl- or tert.-butyl-thio and also includes corresponding pentyl-, hexyl- and heptyl-thio radicals $C_1$–$C_4$-alkylthio is preferred.

$C_1$–$C_7$-alkane sulphinyl or -sulphonyl is especially $C_1$–$C_4$-alkane-sulphinyl or -sulphonyl, such as methane-, ethane-, propane-, isopropane-, n-butane-, sec.-butane- and tert.-butane-sulphinyl or -sulphonyl.

In $C_3$–$C_6$-alkenyl or -alkynyl, the multiple bond is located in a position higher than the α-position $C_3$–$C_4$-alkenyl or -alkynyl, such as allyl and methallyl or propargyl, is preferred.

In $C_2$–$C_8$-alkoxycarbonyl, alkoxy has the meanings given above.

In $C_1$–$C_7$-alkyl- or di-$C_1$–$C_7$-alkyl-carbamoyl, alkyl has the meanings given above.

$C_2$–$C_8$-alkanoyl is, for example, acetyl, propionyl, butyryl, isobutyryl or pivaloyl.$C_2$–$C_5$-alkanoyl is preferred.

The compounds of the formula I, or corresponding tautomeric forms thereof, and their pharmaceutically acceptable acid addition salts have, for example, valuable pharmacological properties. For example, it has been established that the class of compounds according to the invention has a novel action profile The compounds of the formula I, or corresponding tautomeric forms thereof, and their pharmaceutically acceptable salts have been found to be inhibitors of catecholamine-O-methyltransferase (COMT). These properties can be demonstrated in three in vivo test systems, COMT-inhibition in vivo being verified by the reduction in homovan:rllic acid that can be observed in the C. striatum of the rat and by the inhibition of 3-methoxytyramine accumulation after monoamine oxidase-inhibition in the C. striatum of the rat, in each case at a dose of 0.1 mg/kg and above after i.p. administration. Furthermore, within the framework of a single-cell derivation in the narcotised rat, an increase in the firing of locus caeruleus cells can be observed at approximately 3 mg/kg and above.

TEST DESCRIPTIONS

Determination of homovanillic acid (HVA) in the C. striatum of the rat

Striata are removed from rats' brains and stored in a deep-frozen state at −20° C. until they are analysed. The striata are homogenised in pairs in 2 ml of the mobile phase required for the HPLC separation described below This mobile phase contains per extract, as the internal standard, 1000 ng of vanillic acid. Cell fragments are removed by centrifugation. From 50 to 200 μl of the supernatant are injected into a BAS liquid chromatography system (Bioanalytical Systems, W. Lafayette, Ind., USA) which is equipped with a $C_{18}$ μBondapak reversed-phase column (Waters Ass., Milford, USA), with a TL3 electrochemical detector cell and an LC4 monitoring system. The detector cell contains cp$_w$ graphite paste, and the potential is set to +0.85 V against an Ag/Ag Cl reference electrode. The mobile phase, which contains 0.1 mol/liter of citric acid, 0.075 mol/liter of disodium hydrogen phosphate, 2.5% tetrahydrofuran and 0.05 mol/liter of sodium octyl sulphate, is adjusted to pH 3 using hydrochloric acid. The column temperature is brought up to from 28° to 40° C. and the throughput to from 1 to 1.3 ml/min in order to achieve optimum separation. Five animals are used per group.

Determination of
3-methoxytyramine(3-MT)-enrichment after MAO-inhibition by clorgyline Rats to which the test substance was administered perorally or intraperitoneally 5 minutes before the injection of 10 mg/kg of clorgyline (s.c.) are killed thirty minutes later by irradiation with microwaves (10 kW power, 2450 MHz, duration from 1.7 to 1.8 seconds, Pueschner Mikrowellen-Energietechnik, Schwanewede/Bremen, Federal Republic of Germany). When the animals have cooled, the striata are removed and homogenised in a mixture of 2 ml of 0.1 mol/liter of citric acid, 0.075 mol/liter of disodium hydrogen phosphate, 2.5% tetrahydrofuran and 0.05 mmol/liter of sodium octyl sulphate which is adjusted to pH 3 using hydrochloric acid and to which 1000 ng of vanillic acid are added as the internal standard Cell fragments are separated off by centrifugation. From 50 to 200 μl of the supernatant are injected into a BAS liquid chromatography system (Bioanalytical Systems, W. Lafayette, Ind., USA) which is equipped with a $C_{18}$ μBondapak reversed-phase column (Waters Ass., Milford, USA) and a 5100A coulometer detector, Model ESA, with a detector cell, Model 5010 (ESA Inc., Bedford, Mass., USA); potential of the detector 2:+0.45 V, detector 1 disconnected). The mobile phase comprises a citrate/phosphate buffer (prepared by mixing 0.1M citric acid and 0.1M disodium hydrogen phosphate at pH 3) to which 10% ethanol and 1 55 mM/liter of sodium octyl sulphate have been added; the pump speed is 1.3 ml/min.

As a result of the inhibition of COMT, the metabolic decomposition of the catecholamines, for example dopamine, formed in the neurones and released as a result of nerve stimulation is inhibited and the concentration of these amines in the synaptic gap increases. Thus, for example, the cause of depressive phenomena and Parkinson's disease, for example dopamine deficiency, is largely eliminated When the compounds according to the invention are used, an enrichment of S-adenosyl-methionine, which is necessary for methylation, takes place in the neurones at the same time as the inhibition of COMT. It is customarily thought that an increase in the S-adenosyl-methionine concentration brings about an increase in learning ability.

Accordingly, the compounds of the formula I, or corresponding tautomers thereof, and their pharmaceutically acceptable salts can be used, for example, as pharmaceuticals, such as nootropics, antidepressants and anti-Parkinson agents. The invention relates also to the use of the compounds according to the invention for the manufacture of medicaments, especially nootropics, antidepressants and anti-Parkinson agents, and for therapeutic and prophylactic treatment. The commercial formulation of the active ingredients may also be included.

The invention relates especially to compounds of the formula I, to their tautomers and to their salts, in which $R_1$ represents hydrogen or $C_1$-$C_7$-alkyl, one of the radicals $R_2$ and $R_3$ represents hydrogen, $C_1$-$C_7$-alkyl or aryl-$C_1$-$C_7$-alkyl and the other represents $C_1$-$C_7$-alkyl or aryl-$C_1$-$C_7$-alkyl and $R_4$ represents hydrogen or $C_1$-$C_7$-alkyl, $R_5$ represents $C_1$-$C_7$-alkyl and the index n represents 0 or 1.

The invention relates especially to compounds of the formula I, to their tautomers and to their salts, in which $R_1$ represents hydrogen or $C_1$-$C_7$-alkyl, one of the radicals $R_2$ and $R_3$ represents hydrogen, $C_1$-$C_7$-alkyl or aryl- $C_1$-$C_7$-alkyl and the other represents $C_1$-$C_7$-alkyl or aryl-$C_1$-$C_7$-alkyl and $R_4$ represents hydrogen and the index n represents 0.

The invention relates especially to compounds of the formula I, to their tautomers and to their salts, in which $R_1$ represents hydrogen or $C_1$-$C_7$-alkyl, one of the radicals $R_2$ and $R_3$ represents hydrogen, $C_1$-$C_7$-alkyl or phenyl-, naphthyl-, indenyl-, pentalenyl-, azulenyl-, pyrryl-, pyrazolyl-, imidazolyl-, triazolyl-, furyl-, thienyl-, isoxazolyl-, oxazolyl-, oxadiazolyl-, isothiazolyl-, thiazolyl-, thiadiazolyl-, pyridyl-, pyridazinyl-, pyrimidyl-, pyrazinyl- or triazinyl-$C_1$-$C_4$-alkyl and the other represents $C_1$-$C_7$-alkyl or phenyl-, naphthyl-, indenyl-, pentalenyl-, azulenyl-, pyrryl-, pyrazolyl-, imidazolyl-, triazolyl-, furyl-, thienyl-, isoxazolyl-, oxazolyl-, oxadiazolyl-, isothiazolyl-, thiazolyl-, thiadiazolyl-, pyridyl-, pyridazinyl-, pyrimidyl-, pyrazinyl-, or triazinyl-$C_1$-$C_4$-alkyl and $R_4$ represents hydrogen and the index n represents 0.

The invention relates especially to compounds of the formula I, to their tautomers and to their salts, in which one of the radicals $R_2$ and $R_3$ represents hydrogen, $C_1$-$C_7$-alkyl or phenyl- or naphthyl-$C_1$-$C_7$-alkyl and the other represents $C_1$-$C_7$-alkyl or phenyl- or naphthyl-$C_1$-$C_7$-alkyl, phenyl and naphthyl in each case being unsubstituted or mono- or poly-substituted by halogen, $C_1$-$C_7$-alkyl, $C_1$-$C_7$-alkoxy, hydroxy and/or by $C_2$-$C_8$-alkanoyloxy.

The invention relates more especially to compounds of the formula I, to their tautomers and to their salts, in which $R_1$ represents hydrogen or $C_1$-$C_4$-alkyl; such as methyl, on the one hand $R_2$ and $R_3$ each represents, independently of the other, $C_1$-$C_4$-alkyl, such as propyl, or, on the other hand, $R_2$ represents $C_1$-$C_4$-alkyl, such as methyl, and $R_3$ represents phenyl-$C_1$-$C_4$-alkyl, such as 2-phenyl-ethyl, and $R_4$ represents hydrogen and the index n represents 0.

The invention relates more especially to compounds of the formula I, to their tautomers and to their salts, in which $R_1$ represents hydrogen or $C_1$-$C_4$-alkyl, such as methyl, on the one hand $R_2$ and $R_3$ each represents, independently of the other, $C_1$-$C_4$-alkyl, such as propyl, or, on the other hand, $R_2$ represents $C_1$-$C_4$-alkyl, such as methyl, and $R_3$ represents phenyl-$C_1$-$C_4$-alkyl, such as 2-phenylethyl, $R_4$ represents $C_1$-$C_4$-alkyl, such as methyl, and the index n represents 0.

The invention relates more especially to compounds of the formula I, to their tautomers and to their salts, in which $R_1$ and $R_4$ represent hydrogen and each of $R_2$ and $R_3$, independently of the other, represents $C_1$-$C_4$-alkyl, such as propyl, and the index n represents 0.

The invention relates more especially to compounds of the formula I, to their tautomers and to their salts, in which $R_1$ represents hydrogen, $R_4$ represents $C_1$-$C_4$-alkyl, such as methyl, and each of $R_2$ and $R_3$, independently of the other, represents $C_1$-$C_4$-alkyl, such as propyl, and the index n represents 0.

The invention relates more especially to compounds of the formula I, to their tautomers and to their salts, in which $R_1$ represents methyl, $R_4$ represents hydrogen and each of $R_2$ and $R_3$, independently of the other, represents $C_1$-$C_4$-alkyl, such as propyl, and the index n represents 0.

The invention relates especially to the novel compounds mentioned in the Examples and to processes for their manufacture.

The invention relates also to processes for the manufacture of the compounds according to the invention. The manufacture of compounds of the formula I, their tautomers and their salts is carried out in a manner known per se and is, for example, characterised in that (a) a compound of the formula

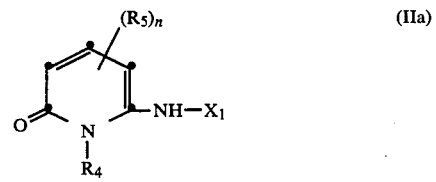

or a tautomer thereof is reacted with a compound of the formula

in which one of the radicals $X_1$ and $X_2$ represents a group of the formula —CO—$R_1$ and the other represents hydrogen or a group of the formula —CO—$Z_1$ in which $Z_1$ represents a removable radical, or tautomers, salts and/or acetals thereof, or (b) in a compound of the formula

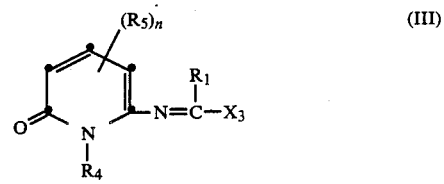

or a tautomer and/or salt thereof in which $X_3$ represents a radical that can be converted into

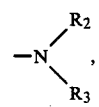

$X_3$ is converted into

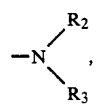

or (c) for the manufacture of compounds of the formula I, a tautomer and salt thereof in which $R_4$ represents hydrogen, in a compound of the formula

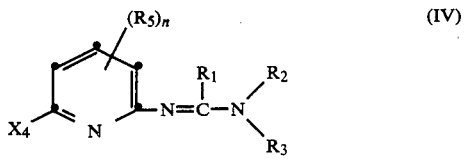

or a salt thereof in which $X_4$ represents protected hydroxy, the hydroxy-protecting group is removed, or (d) a compound of the formula

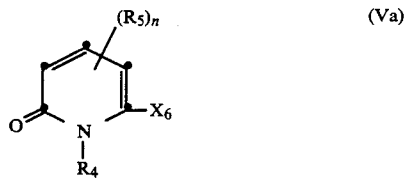

or a tautomer or salt thereof is reacted with a compound of the formula

or a tautomer or a salt thereof in which $X_6$ represents the group $-N=CR_1-NH-X_5$ and $X_7$ represents hydrogen, or $X_6$ represents $-NH_2$ and $X_7$ represents the group $-CR_1=N-X_5$, and $X_5$ represents a leaving group, and, if desired, a compound obtainable according to the process or by other means is converted into a different compound of the formula I or a tautomer thereof, an isomeric mixture obtainable according to the process is separated into its components, a free compound of the formula I obtainable according to the process or a tautomer thereof is converted into a salt, and/or a salt obtainable according to the process is converted into the free compound of the formula I or a tautomer thereof or into a different salt.

The reactions described hereinbefore and hereinafter in the variants are carried out in a manner known per se, for example in the absence, or customarily in the presence, of a suitable solvent or diluent or a mixture thereof, the reactions being carried out, as necessary, while cooling, at room temperature or while heating, for example in a temperature range of approximately from $-80°$ up to the boiling temperature of the reaction medium, preferably from approximately $-10°$ to approximately $+100°$ C., and, if necessary, in a closed vessel, under pressure, in an inert gas atmosphere and/or under anhydrous conditions.

The starting materials of the formulae IIa and IIb, III, IV and Va and Vb given hereinbefore and hereinafter which were developed for the manufacture of the compounds of the formula I, their tautomers and their salts are in some cases known or can likewise be manufactured according to methods known per se, for example analogously to the process variants described above.

Salts of the starting materials of the formulae IIa, IIb, III, IV, Va and Vb are especially corresponding acid addition salts since these starting compounds have at least one basic centre.

Suitable acids for salt formation are, for example, strong inorganic acids, such as mineral acids, for example sulphuric acid, phosphoric acid or hydrohalic acids, strong organic carboxylic acids, such as $C_1-C_4$-alkanecarboxylic acids, for example glacial acetic acid, such as optionally unsaturated dicarboxylic acids, for example oxalic, malonic, maleic or fumaric acid, or such as hydroxycarboxylic acids, for example tartaric acid or citric acid, or sulphonic acids, such as $C_1-C_4$-alkanesulphonic acid or optionally substituted benzenesulphonic acid, for example methane- or p-toluene-sulphonic acid.

The 2-oxo-dihydro-pyridine derivatives of the formulae IIa, III and Va may, for example, likewise be in the form of corresponding tautomeric 2-hydroxypyridines.

Acetals of compounds of the formulae IIa and IIb in which one of the radicals $X_1$ and $X_2$ represents the group of the formula $-CO-R_1$ and the other represents hydrogen are compounds in which the carbonyl function has been acetalised or ketalised with a monohydric or dihydric aliphatic alcohol, such as $C_1-C_7$-alkanol or $C_2-C_5$-alkanediol.

Variant (a):

A removable radical $Z_1$ is, for example, reactive esterified hydroxy, optionally etherified hydroxy or optionally etherified mercapto Reactive esterified hydroxy is especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, optionally substituted, for example halo-substituted, $C_1-C_7$-alkanesulphonyloxy, for example methane- or trifluoromethane-sulphonyloxy, $C_5-C_7$-cycloalkanesulphonyloxy, for example cyclohexanesulphonyloxy, or benzenesulphonyloxy optionally substituted, for example, by $C_1-C_7$-alkyl or by halogen, for example p-bromophenyl- or p-toluene-sulphonyloxy. Etherified hydroxy is, for example, optionally substituted, for example phenyl-substituted, $C_1-C_7$-alkoxy, such as methoxy, ethoxy or benzyloxy, while, for example, $C_1-C_7$-alkylthio, such as methyl- or ethyl-thio, is suitable as etherified mercapto. $Z_1$ represents preferably halogen, such as chlorine, or $C_1-C_4$-alkoxy, such as methoxy or ethoxy.

The reaction of compounds of the formulae IIa and IIb in which one of the radicals $X_1$ and $X_2$ represents a group of the formula $-CO-R_1$ and the other represents hydrogen is carried out especially in the presence of a condensation agent, such as a dehydrating agent or an anhydride of an inorganic acid.

There may be used as dehydrating agents especially carbodiimides, for example N,N'-di-$C_1-C_4$-alkyl- or N,N'-di-$C_5-C_7$-cycloalkyl-carbodiimide, such as N,N'-dicyclohexylcarbodiimide, advantageously with the addition of N-hydroxysuccinimide or optionally substituted, for example halo-, $C_1-C_7$-alkyl- or $C_1-C_7$-alkoxy-substituted, N-hydroxybenzotriazole or N-hydroxy-5-norbornene-2,3-dicarboxamide, also suitable carbonyl compounds, for example N,N-carbonyldiimidazole, suitable 1,2-oxazolium compounds, for example 2-ethyl-5-phenyl-1,2-oxazolium 3'-sulphonate or 2-tert.-butyl-5-methyl-isoxazolium perchlorate, suitable acylamino compounds, for example 2-ethoxy-1-ethoxycarbonyl-1,2-dihydroquinoline, or suitable phosphorylcyanamides or phosphorylazides, for example diethylphosphorylcyanamide or diphenylphosphorylazide, also triphenylphosphine disulphide or 1-$C_1-C_4$-alkyl-2-halopyridinium halides, for example 1-methyl-2-chloro-pyridinium iodide.

There may be mentioned as examples of anhydrides of inorganic acids phosphorus pentoxide, phosphorus oxyhalides, such as phosphorus oxychloride, phosgene or thionyl chloride.

It is preferable to use compounds of the formula IIa and IIb in which one of the radicals $X_1$ and $X_2$ represents a group of the formula —CO—$R_1$ that is in acetalised or ketalised form and the other represents hydrogen.

In the reaction of compounds of the formulae IIa and IIb in which one of the radicals $X_1$ and $X_2$ represents a group of the formula —CO—$R_1$ and the other represents a group of the formula —CO—$Z_1$ in which $Z_1$ represents a removable radical, it is preferable to use those starting materials in which $Z_1$ represents halogen, such as chlorine. The reaction is carried out especially while heating, for example in a temperature range of from 50° C. up to the boiling temperature of the reaction medium.

The starting materials of the formulae IIa and IIb are in some cases known and can be manufactured in a manner known per se, for example by N-acylation of an amine of the formula

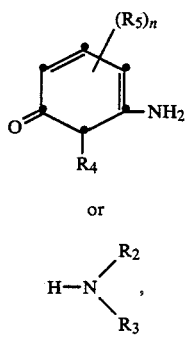

respectively.
Variant (b):
A radical $X_3$ that can be converted into

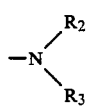

is, for example, amino.

Corresponding compounds of the formula III can be alkylated, for example, with an alkylating agent on which $R_2$ and $R_3$ are based, such as an alkylating agent derived from $R_2$—OH and $R_3$—OH or from a reactive esterified derivative thereof or from a corresponding carbonyl compound. Such alkylating reagents are, for example, corresponding halides, sulphates or sulphonates, for example of the formulae $R_2$—$Z_2$ and $R_3$—$Z_2$ in which $Z_2$ represents, for example, halogen or sulphonyloxy, such as $C_1$-$C_7$-alkanesulphonyloxy or optionally substituted benzenesulphonyloxy, for example methane- or p-toluene-sulphonyloxy.

The alkylation of corresponding compounds of the formula III is carried out especially in the presence of a base.

Suitable bases are, for example, alkali metal hydroxides, hydrides, amides, alkoxides, carbonates, triphenylmethylides, di-$C_1$-$C_7$-alkylamides, amino-$C_1$-$C_7$-alkylamides or $C_1$-$C_7$-alkylsilylamides, naphthaleneamines, $C_1$-$C_7$-alkylamines, basic heterocycles, ammonium hydroxides and carbocyclic amines. There may be mentioned by way of example: lithium hydroxide, sodium hydroxide, hydride, amide or ethoxide, potassium tert.-butoxide or carbonate, lithium triphenyl methylide or diisopropylamide, potassium 3-(aminopropyl)-amide or bis-(trimethylsilyl)-amide, dimethylaminonaphthalene, di- or triethylamine, pyridine, benzyltrimethylammonium hydroxide, 1,5-diaza-bicyclo[4.3.0]non-5-ene (DBN) and 1,8-diaza-bicyclo[5.4.0]undec-7-ene (DBU).

If, for example, carbonyl compounds are used as the alkylating agents, the reaction can be carried out, for example, in the presence of a reducing agent, for example with formic acid and formamide analogously to the Leuckart-Wallach reaction.

$X_3$ in the formula III may also represent a leaving group, such as reactive esterified hydroxy, optionally etherified hydroxy or optionally etherified mercapto. Reactive esterified hydroxy is especially hydroxy esterified by a strong inorganic acid or organic sulphonic acid, for example halogen, such as chlorine, bromine or iodine, sulphonyloxy, such as hydroxysulphonyloxy, halosulphonyloxy, for example fluorosulphonyloxy, optionally substituted, for example halo-substituted, $C_1$-$C_7$-alkanesulphonyloxy, for example methane- or trifluoromethane-sulphonyloxy, $C_5$-$C_7$-cycloalkanesulphonyloxy, for example cyclohexanesulphonyloxy, or benzenesulphonyloxy optionally substituted, for example, by $C_1$-$C_7$-alkyl or by halogen, for example p-bromophenyl- or p-toluene-sulphonyloxy. Etherified hydroxy is, for example, optionally substituted, for example phenylsubstituted, $C_1$-$C_7$-alkoxy, such as methoxy, ethoxy or benzyloxy, while, for example, $C_1$-$C_7$-alkylthio, such as methyl- or ethyl-thio, is suitable as etherified mercapto. $X_3$ represents preferably halogen, such as chlorine, or $C_1$-$C_4$-alkoxy, such as methoxy or ethoxy.

Corresponding compounds of the formula III in which $X_3$ represents a leaving group are reacted with an amine of the formula

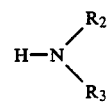

or a salt thereof.

The starting material of the formula III in which $X_3$ represents amino can be obtained, for example, by reacting a compound of the formula

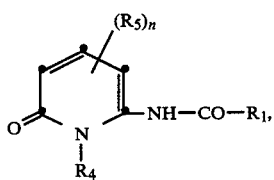

a tautomer or a salt thereof, with ammonia.

Starting compounds of the formula III in which $X_3$ represents a leaving group can be obtained, for example, by first treating a compound of the formula IIIa with a halogenating reagent, such as phosgene, ($X_3$=halogen) and then reacting the corresponding resulting compounds of the formula III, for example, with a desired alcohol or mercaptan.

Variant (c):

There come into consideration as protected hydroxy $X_4$, for example, esterified, etherified or acetalised hydroxy, such as acyloxy, silyloxy, optionally substituted alkoxy or tetrahydropyranyloxy. The acyl radical in acyloxy represents, for example, optionally substituted, for example halo-substituted, $C_2$–$C_5$-alkanoyl or benzoyl, such as acetyl, monochloroacetyl or benzoyl, or $C_2$–$C_5$-alkoxycarbonyl optionally substituted by a phenyl radical, such as ethoxy-, tert.-butoxy-, benzyloxy-, 2-bromobenzyloxy- or 4-methoxybenzyloxycarbonyl Silyl in silyloxy is, for example, tri-$C_1$–$C_4$-alkyl-silyl, such as trimethylsilyl or tert.-butyl-dimethylsilyl. Optionally substituted alkyl as in the case of corresponding alkoxy represents, for example, $C_1$–$C_4$-alkyl optionally substituted, for example, by a phenyl radical, such as tert.-butyl, benzyl or 3-bromobenzyl.

The removal of the particular hydroxy-protecting group is carried out in a manner known per se, for example by hydrolysis, acidolysis, reduction, hydrazinolysis or by treatment with thiourea.

For example, $C_2$–$C_5$-acetyl, $C_2$–$C_5$-alkanoyl, benzoyl, ethoxycarbonyl, benzoyloxycarbonyl, tetrahydropyranyl or silyl radicals are removed by hydrolysis, especially in the presence of an acid or, more especially, in the presence of a base, while, for example, 2-bromobenzyloxycarbonyl, benzyloxycarbonyl, benzyl, 3-bromobenzyl or tert.-butyl radicals are removed by acidolysis, for example by treatment with a strong acid, such as hydrochloric acid, hydrobromic acid/glacial acetic acid, hydrofluoric acid or trifluoroacetic acid. It is also possible to free hydroxy from benzyloxy by reduction, for example by catalytic hydrogenation, advantageously in the presence of a hydrogenation catalyst, or by treatment with sodium in liquid ammonia The compounds of the formula IV can be obtained, for example, by reacting compounds of the formula

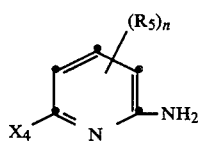

(IVa)

or a salt thereof with a compound of the formula

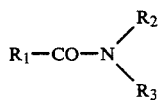

(IVb)

or an acetal or ketal thereof, the procedure being as in Process variant (a).

Variant (d):

Suitable as the leaving group $X_5$ is preferably cyano.

The starting material of the formula Vb in which $X_7$ represents the group —CR=N—$X_5$ in which $X_5$ represents cyano can be obtained, for example, by reacting a compound of the formula

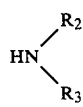

(IIc)

or a salt thereof with a compound of the formula

(Vc)

in which $Z_2$ represents a leaving group, for example $C_1$–$C_4$-alkoxy.

For the manufacture of compounds of the formula Va in which $X_6$ represents —N=$CR_1$—NH—$X_5$ in which $X_5$ represents cyano, there is used as starting material, for example, a compound of the formula IIIa which is reacted with a compound of the formula

(Vd), optionally while heating.

The invention relates also to the novel compounds obtainable according to the above process variants.

A compound of the formula I obtainable according to the invention or by other means, a tautomer or salt thereof, can be converted in a manner known per se into a different compound of the formula I or into a tautomeric form thereof.

If one of the radicals $R_2$ and $R_3$ represents hydrogen, corresponding compounds of the formula I, their tautomers or salts can be N-alkylated in a manner known per se; carbamoyl $R_5$ can likewise be N-alkylated The (aryl-)$C_1$–$C_7$-alkylation is carried out, for example, with a reactive ester of an (aryl-)$C_1$–$C_7$-alkyl halide, for example the bromide or iodide, an (aryl-)$C_1$–$C_7$-alkylsulphonate, for example -methanesulphonate or -p-toluenesulphonate, or a di-$C_1$–$C_7$-alkyl sulphate, for example dimethyl sulphate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, although more strongly basic condensation agents, such as alkali metal. amides, hydrides or alcoholates, for example sodium amide, sodium hydride or sodium methoxide, may be necessary.

Likewise, the compounds of the formula I, their tautomers or salts in which at least one of the radicals $R_2$ and $R_3$ is other than hydrogen can be transamidated by treatment with a corresponding amine.

Compounds of the formula I, tautomers or salts thereof in which $R_4$ represents hydrogen can be alkylated with the aid of a suitable alkylating agent to form compounds of the formula I in which $R_4$ represents (aryl-)$C_1$–$C_7$-alkyl.

Furthermore, hydroxy groups which may be present can be esterified, for example converted into $C_2$–$C_8$-alkanoyloxy by treatment with a $C_2$–$C_7$-alkane-carboxylic acid anhydride or halide or converted by reaction with a reactive ester, especially a hydrobromic or hydrochloric acid ester, of a $C_1$–$C_7$-alkanol into corresponding etherified hydroxy. Conversely, in esterified or etherified hydroxy groups, such as $C_2$–$C_8$-alkanoyloxy or $C_1$–$C_7$-alkoxy, it is possible to free the hydroxy group(s) by solvolysis, preferably under acidic conditions. In an analogous manner it is also possible to hydrolyse acylated hydroxy to hydroxy.

Thio in $C_1$–$C_7$-alkylthio ($R_5$) can be oxidised, for example in customary manner, to form corresponding sulphinyl or sulphonyl. There come into consideration as suitable oxidation agents for the oxidation to the sulphoxide stage, for example, inorganic per-acids, such as per-acids of mineral acids, for example periodic acid or persulphuric acid, organic per-acids, such as corresponding percarboxylic or persulphonic acids, for example performic, peracetic, trifluoroperacetic, p-nitroperbenzoic, m-chloroperbenzoic or perbenzoic acid or p-toluene-persulphonic acid, or mixtures of hydrogen peroxide and acids, for example a mixture of hydrogen peroxide and acetic acid. The oxidation is often carried out in the presence of suitable catalysts, and, as catalysts, there may be mentioned suitable acids, such as optionally substituted carboxylic acids, for example acetic acid or trifluoroacetic acid, or transition metal oxides, such as oxides of elements of sub-group V or VI, for example vanadium, molybdenum or tungsten oxide. The oxidation is advantageously carried out under mild conditions. The oxidation to the sulphone stage can also be carried out in an analogous manner using dinitrogen tetroxide as the catalyst in the presence of oxygen at low temperatures, as can the direct oxidation of thio to sulphonyl, but in that case the oxidation agent is generally used in excess.

A cyano group ($R_5$) can be converted into the carbamoyl group, for example, by hydrolysis, preferably under acidic or basic conditions, for example in the presence of an alkali metal hydroxide, and, if desired, in the presence of hydrogen peroxide in an aqueous-alcoholic solvent.

Likewise, the substituent cyano can be converted into $C_2$–$C_8$-alkoxycarbonyl ($R_5$), for example, by treatment with a $C_1$–$C_7$-alkanol, for example in the presence of an acid, such as hydrochloric acid.

In compounds of the formula (I) that have an esterified or amidated carboxy group ($R_5$) as substituent, that group can be converted into a free carboxy group, for example, by hydrolysis, for example in the presence of a basic agent, or in the presence of an acidic agent, such as a mineral acid.

Furthermore, in compounds of the formula (I) that have a carboxy group ($R_5$) as substituent, that group can be converted into an esterified carboxy group ($R_5$), for example, by treatment with an alcohol, such as a lower alkanol, in the presence of a suitable esterifying agent, such as an acidic reagent, for example an inorganic or organic acid or a Lewis acid, for example zinc chloride, or in the presence of water-binding condensation agent, for example a carbodiimide, such as N,N'-dicyclohexylcarbodiimide, or by treatment with a diazo reagent, such as a diazo-lower alkane, for example diazomethane. An esterified carboxy group ($R_5$) can also be obtained if compounds of the formula I in which the carboxy group ($R_5$) is in free form or in salt form, such as ammonium salt form or metal salt form, for example alkali metal, such as sodium or potassium, salt form, are treated with a reactive ester of a $C_1$–$C_7$-alkyl halide, for example methyl or ethyl chloride, bromide or iodide, or with an organic sulphonic acid ester, such as a corresponding $C_1$–$C_7$-alkyl ester, for example methanesulphonic acid or p-toluenesulphonic acid methyl ester or ethyl ester.

Compounds of the formula (I) that have an esterified carboxy group ($R_5$) as substituent can be converted into other ester compounds of the formula (I) by transesterification, for example, by treatment with an alcohol, generally one that is higher than the alcohol corresponding to the esterified carboxy group in the starting material, in the presence of a suitable transesterification agent, such as a basic agent, for example an alkali metal $C_1$–$C_7$-alkanoate, $C_1$–$C_7$-alkoxide or cyanide, such as sodium acetate, methoxide, ethoxide, tert.-butoxide or cyanide, or a suitable acidic agent, optionally with removal of the resulting alcohol, for example by distillation It is also possible to start from corresponding so-called activated esters of the formula (I) that contain as substituent an activated esterified carboxy group (see below) and to convert this group into a different ester by treatment with a $C_1$–$C_7$-alkanol.

Compounds of the formula (I) that contain an amidated carboxy group as substituent can advantageously also be obtained from the corresponding acid and ester compounds of the formula (I) that have an optionally esterified carboxy group as substituent. For example, compounds of the formula (I) that have a free carboxy group can be reacted with urea at elevated temperatures with a formamide, for example dimethylformamide, in the presence of a suitable condensation agent, such as phosphorus pentoxide, at elevated temperatures, or with an amine in the presence of a suitable condensation agent, such as a carbodiimide, for example N,N'-diethylcarbodiimide, also a phosphine, such as triphenylphosphine (for example together with bis-2-pyridyl disulphide), or a silane, such as trichlorosilane (for example together with pyridine), to obtain the corresponding amide compounds of the formula (I) that contain an amidated carboxy group ($R_5$) as substituent. It is also possible to obtain these compounds from compounds of the formula (I) that have a carboxy group ($R_5$) in salt form as substituent, for example by dehydrating a corresponding ammonium salt, for example by treatment with a dehydrating agent, such as phosphorus pentoxide, or by reacting a corresponding alkali metal salt, for example a sodium salt, with an amine, preferably in the presence of a suitable condensation agent, such as phenylphosphonic acid dichloride.

In compounds of the formula (I) that contain the carboxy group ($R_5$) as substituent, it is also possible to convert that group first into a reactive derivative, such as an anhydride, including a mixed anhydride, such as an acid halide, for example an acid chloride (for example by treatment with a thionyl halide, for example thionyl chloride) or an anhydride with a formic acid ester, for example a $C_1$–$C_7$-alkyl ester (for example by treatment of a salt, such as an ammonium or alkali metal salt, with a haloformic acid ester, such as a chloroformic acid ester, such as a $C_1$–$C_7$-alkyl ester) or into an activated ester, such as a cyanomethyl, nitrophenyl, for example 4-nitrophenyl, or polyhalophenyl, for example pentachlorophenyl, ester (for example by treatment with a corresponding hydroxy compound in the presence of a suitable condensation agent, such as N,N'-dicyclohexylcarbodiimide), and such a reactive derivative can then be reacted with an amine to produce amide compounds of the formula (I) that have an amidated carboxy group as substituent. These compounds can be obtained direct or via intermediate compounds; for example, an activated ester, such as a 4-nitrophenyl ester, of a compound of the formula I having a carboxy group can first be reacted with a 1-unsubstituted imidazole and the resulting 1-imidazolylcarbonyl compound can be reacted with the amine It is, however, also possible to react other, non-activated esters, such as $C_1$–$C_7$-alkyl esters of compounds of the formula (I) having, for example, $C_2$–$C_8$-alkoxycarbonyl ($R_5$) as substituent, with amines.

If the compounds of the formula (I) contain $C_3$–$C_6$-alkenyl or $C_3$–$C_6$-alkynyl groupings, these can be converted in a manner known per se into corresponding saturated radicals. For example, the hydrogenation of multiple bonds is carried out by catalytic hydrogenation in the presence of hydrogenation catalysts, there being suitable for this purpose, for example, noble metals or their derivatives, for example oxides, such as nickel, Raney nickel, palladium and platinum oxide, which may optionally be supported on carriers, for example on carbon or calcium carbonate The hydrogenation can be carried out preferably at pressures of from 1 to approximately 100 atm.

Salts of compounds of the formula (I) or their tautomers can be manufactured in a manner known per se. For example, acid addition salts of compounds of the formula (I) or tautomers thereof are obtained by treatment with an acid or a suitable ion-exchange reagent. Salts can be converted in customary manner into the free compounds: acid addition salts, for example, by treatment with a suitable basic agent.

Depending on the procedure and the reaction conditions, the compounds according to the invention having salt-forming, especially basic, properties may be obtained in free form or preferably in the form of salts.

Owing to the close relationship between the novel compound in free form and in the form of its salts, hereinbefore and hereinafter there is to be understood by the free compound or its salts, where appropriate with regard to meaning and purpose, optionally also the corresponding salts or the free compound, respectively.

The novel compounds, including the salts of salt-forming compounds, may also be obtained in the form of their hydrates or may include other solvents used for crystallisation.

Depending on the starting materials and procedures chosen, the novel compounds may be in the form of one of the possible isomers or in the form of mixtures thereof, for example depending on the number of asymmetric carbon atoms, in the form of pure optical isomers, such as antipodes, or in the form of isomeric mixtures, such as racemates, diastereoisomeric mixtures or mixtures of racemates.

Resulting mixtures of racemates can be separated in known manner into the pure isomers or racemates on the basis of the physico-chemical differences between the components, for example by fractional crystallisation.

Resulting racemates can also be split into the optical antipodes according to known methods, for example by recrystallisation from an optically active solvent, chromatography on chiral adsorbents, with the aid of suitable microorganisms, by cleavage with specific, immobilised enzymes, by means of the formation of inclusion compounds, for example using chiral Crown ethers, with only one enantiomer being complexed, or by conversion into diastereoisomeric salts, for example by reacting a basic end product racemate with an optically active acid, such as a carboxylic acid, for example tartaric or malic acid, or sulphonic acid, for example camphorsulphonic acid, and separating the diastereoisomeric mixture obtained in that manner into the diastereoisomers, for example on the basis of their differing solubilities, from which diastereoisomers the desired enantiomer can be freed by the action of suitable agents Advantageously, the more active enantiomer is isolated.

The invention relates also to those forms of the process according to which a compound obtainable as an intermediate at any stage of the process is used as starting material and the remaining steps are carried out or a starting material is used in the form of a derivative or salt and/or in the form of its racemates or antipodes, or, especially, is formed under the reaction conditions.

The starting materials used in the process of the present invention are preferably those which result in the compounds described at the beginning as being especially valuable The invention relates also to novel starting materials which have been developed specifically for the manufacture of the compounds according to the invention, their use and processes for their manufacture, the variables $R_1$, $R_2$, $R_3$, $R_4$ and $R_5$ having the meanings given for the compound groups of the formula I or tautomers thereof that are preferred in each case. Compounds of the formula III, their tautomers and salts in which $X_3$ represents amino are especially preferred as starting materials.

The invention relates also to the use of the compounds of the formula (I) or tautomers thereof or pharmaceutically acceptable salts of such compounds having salt-forming properties, especially as pharmacological active substances having especially nootropic, antidepressive and anti-Parkinson action. They can be used, preferably in the form of pharmaceutically acceptable preparations, in a method for the prophylactic and/or therapeutic treatment of the animal or human body, especially as nootropics, antidepressants and agents for the treatment of Parkinson's syndrome.

The invention relates also to pharmaceutical preparations that contain the compounds according to the invention or pharmaceutically acceptable salts thereof as active ingredients, and to processes for their manufacture.

The pharmaceutical preparations according to the invention which contain the compounds according to the invention or pharmaceutically acceptable salts thereof are for enteral, such as oral and also rectal, administration and for parental administration to (a) warm-blooded animal(s), the pharmacological active ingredient being present on its own or together with a pharmaceutically acceptable carrier. The daily dosage of the active ingredient depends on the age and the individual condition and also on the mode of administration.

The novel pharmaceutical preparations contain, for example, from approximately 10% to approximately 80%, preferably from approximately 20% to approximately 60%, active ingredient Pharmaceutical preparations according to the invention for enteral or parental administration are, for example, those in dosage unit form, such as dragées, tablets, capsules or suppositories, and also ampoules. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary, after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using corn, wheat, rice or potato starch, gelatine, tragacanth, methylcellulose and/or polyvinylpyrrolidone, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearat and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Colourings or pigments can be added to the tablets or dragée coatings, for example for identification purposes or to indicate different doses of active ingredient.

Further orally administrable pharmaceutical preparations are dry-filled capsules consisting of gelatine and also soft, sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, it being possible also to add stabilisers.

As rectally administrable pharmaceutical preparations there come into consideration, for example, suppositories which consist of a combination of the active ingredient with a suppository base. Suitable suppository bases are, for example, natural or synthetic triglycerides, paraffin hydrocarbons, polyethylene glycols and higher alkanols. It is also possible to use gelatine rectal capsules which contain a combination of the active ingredient with a base material. As base materials there come into consideration, for example, liquid triglycerides, polyethylene glycols and paraffin hydrocarbons.

Especially suitable for parenteral administration are aqueous solutions of an active ingredient in water-soluble form, for example a water-soluble salt, also suspensions of the active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and, optionally, also stabilisers.

The dosage of the active ingredient depends on the species of warm-blooded animal, the age and individual condition and also on the mode of administration. In normal circumstances, for a warm-blooded animal weighing approximately 75 kg, in the case of oral administration, an approximate daily dosage of from approximately 150 mg to approximately 1500 mg, advantageously in several equal partial doses, is to be recommended.

The following Examples illustrate the invention described hereinbefore, but are not intended to limit its scope in any way Temperatures are given in degrees Celsius.

EXAMPLE 1:

8.3 g (76 mmol) of 6-amino-2-hydroxypyridine and 20 g (114 mmol) of N,N-di-n-propylformamide dimethyl acetal are placed in 70 ml of xylene under argon. .The whole is heated at 100° for ½ hour while stirring It is then allowed to cool, is concentrated by evaporation under a water-jet vacuum and the residue is filtered over 10 times the amount of Florisil using methylene chloride. The fractions containing the product are concentrated by evaporation and then crystallised from n-hexane. N-(2-hydroxy-6-pyridyl)-N',N'-di-n-propylformamidine and N-(2-pyridon-6-yl)-N',N'-di-n-propylformamidine having a melting point of 102°–104° are obtained.

For conversion into the methanesulphonate, the free base is dissolved in methylene chloride and then methanesulphonic acid is added until a pH of 3 is reached. Ether is then added while stirring, the product crystallising out spontaneously The crystals are filtered off with suction, washed well with ether and dried under a high vacuum There are thus obtained N-(2-hydroxy-6-pyridyl)-N',N'-di-n-propylformamidine methanesulphonate

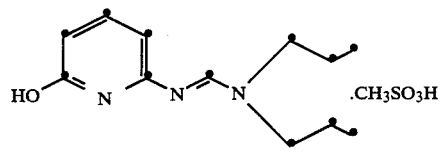

and N-(2-pyridon-6-yl)-N',N'-di-n-propylformamidine methanesulphonate

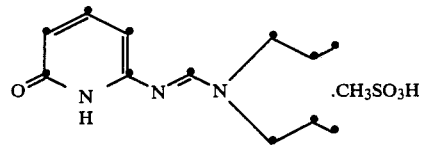

having a melting point of 160°–162°.

EXAMPLE 2:

Analogously to Example 1, N-(2-hydroxy-6-pyridyl)-N',N'-dimethylformamdine and N-(2-pyridon-6-yl)-N',N'-dimethylformamidine having a melting point of 159°–161° can be manufactured; starting from 3.3 g (30 mmol) of 6-amino-2-hydroxypyridine and 5.4 g (45 mmol) of N,N-dimethylformamide dimethyl acetal in 30 ml of xylene.

EXAMPLE 3:

Analogously to Example 1, N-(2-hydroxy-6-pyridyl)-N'-methyl-N'-butylformamidine and N-(2-pyridon-6-yl)-N'-methyl-N'-butylformamidine having a melting point of 85°–86° can be obtained; starting from 3 g (27 mmol) of 6-amino-2-hydroxypyridine and 6.6 g (41 mmol) of N-methyl-N-butylformamide dimethyl acetal in 30 ml of toluene.

EXAMPLE 4:

Analogously to Example 1, N-(2-hydroxy-6-pyridyl)-N'-methyl-N'-(2-phenylethyl)-acetamidine dihydrochloride and N-(2-pyridon-6-yl)-N'-methyl-N'-(2-phenylethyl)-acetamidine dihydrochloride having a melting point of 177°–179° are obtained; starting from 4 g (24 mmol) of N-(2-hydroxy-6-pyridyl)acetimidic acid methyl ester and 4.9 g (36 mmol) of methylphenylethylamine in 20 ml of xylene The starting material can be manufactured as follows:

4.4 g (40 mmol) of 6-amino-2-hydroxypyridine are heated under reflux for 12 hurs in 30 ml of orthoacetic acid trimethyl ester The reaction mixture is then concentrated by evaporation Ether is added to the residue while stirring, the product crystallising out spontaneously. The product is filtered off with suction and dried under a high vacuum. N-(2-hydroxy-6-pyridyl)-acetimidic acid methyl ester having a melting point of 128°–129° is thus obtained.

EXAMPLE 5:

Analogously to Example 4, N-(2-hydroxy-6-pyridyl)-N',N'-di-n-propylacetamidine and N-(2-pyridon-6-yl)-N',N'-di-n-propylacetamidine having a melting point of 140°–141° can be obtained; starting from 2 g (12 mmol) of N-(2-hydroxy-6-pyridyl)acetimidic acid methyl ester and 1 8 g (18 mmol) of di-n-propylamine in 20 ml of xylene.

EXAMPLE 6:

A solution of 4.5 g (20.3 mmol) of N-(2-hydroxy-6-pyridyl)-N',N'-di-n-propylformamidine in 15 ml of absolute tetrahydrofuran is added dropwise, while stirring, at room temperature and under argon, to a suspension of 1 1 g (22.4 mmol) of NaH (50% dispersion in mineral oil) in 30 ml of absolute tetrahydrofuran. Stirring is continued for a further 15 minutes at that temperature and then a solution of 1.4 ml (22.4 mmol) of methyl iodide in 5 ml of tetrahydrofuran is added. The reaction mixture is stirred for 24 hours at room temperature. It is then diluted with ethyl acetate and washed once with water. The organic phase is separated off, dried and concentrated by evaporation The resulting crude product is then purified chromatographically on silica gel. Half an equivalent of fumaric acid in ether is added to the purified product which is then crystallised out by the subsequent addition of petroleum ether N-(1-methyl-2-pyridon-6-yl)-N',N'-di-n-propylformamidine hemifumarate having a melting point of 92°–94° is obtained.

EXAMPLE 7:

At −60° and while stirring, 1.2 g (10 mmol) of BCl$_3$ are slowly metered into a solution of 2.7 g (10 mmol) of N-(2-methoxy-6-pyridyl)-N',N'-di-n-propylformamidine hydrochloride in methylene chloride. The whole is then stirred for a further 30 minutes at that temperature. It is then allowed to warm up to 0° and, after a further one hour, 15 ml of absolute methanol are added carefully. The reaction mixture is then poured onto ice-water, rendered alkaline with 2N sodium hydroxide solution and extracted twice with methylene chloride. The organic phases are combined, dried over Na$_2$SO$_4$, filtered over a layer of Florisil and then concentrated by evaporation. The resulting crude product is crystallised from ether/petroleum ether. N-(2-hydroxy-6-pyridyl)-N',N'-di-n-propylformamidine and N-(2-pyridon-6-yl)-N',N'-di-n-propylformamidine having a melting point of 102°–104° are obtained.

The starting material, N-(2-methoxy-6-pyridyl)-N',N'-di-n-propylformamidine hydrochloride, which has a melting point of 148°–149°, can be manufactured analogously to Example 1; starting from 1.24 g (10 mmol) of 2-amino-6-methoxypyridine and 2.63 g (15 mmol) of N,N-di-n-propylformamide dimethyl acetal in 20 ml of xylene.

EXAMPLE 8:

In a manner analogous to that described in any one of Examples 1 to 7, it is possible to manufacture:

N-(1-methyl-2-pyridon-6-yl)-N',N'-dipropylacetamidine,

N-(1-benzyl-2-pyridon-6-yl)-N',N'-dipropylformamidine,

N-(2-pyridon-6-yl)-N'-propylacetamidine and N-(2-hydroxy-6-pyridyl)-N'-propylacetamidine, N-(2-pyridon-6-yl)-N'-ethyl-N'-isopropylformamidine and N-(2-hydroxy-6-pyridyl)-N'-ethyl-N'-isopropylformamidine, N-(2-pyridon-6-yl)-N',N'-dipropylpropionamidine and N-(2-hydroxy-6-pyridyl)-N',N'-dipropylpropionamidine, N-(1-propyl-2-pyridon-6-yl)-N',N'-dipropylformamidine.

EXAMPLE 9:

Analogously to Example 6, it is possible to manufacture N-(1-propyl-2-pyridon-6-yl)-N',N'-di-n-propylformamidine, a viscous oil of R$_f$=0.43 (toluene/ethanol/conc. aqueous NH$_3$=90:20:1).

There is used as starting material 3 g (14 mmol) of N-(2-hydroxy-6-pyridyl)-N',N'-di-n-propylformamidine and N-(2-pyridon-6-yl)-N',N'-di-n-propylformamidine, 710 mg (15 mmol) of NaH in the form of a 50% dispersion in mineral oil and 1.5 ml (15 mmol) of n-propyl iodide in 30 ml of absolute tetrahydrofuran. In contrast to Example 6, the reaction is carried out for 56 hours under reflux.

EXAMPLE 10:

In a manner analogous to that described in Example 6, N-(1-methyl-2-pyridon-6-yl)-N',N'-di-n-propylacetamidine can be manufactured. It is obtained in the form of a viscous oil, R$_f$=0.28 (methylene chloride/methanol/conc. aqueous NH$_3$=300:10:1).

There is used as starting material 1 g (4.4 mmol) of N-(2-hydroxy-6-pyridyl)-N',N'-di-n-propylacetamidine and N-(2-pyridon-6-yl)-N',N'-di-n-propylacetamidine, 230 mg (4.6 mmol) of NaH (50% dispersion) and 290 μl (4.6 mmol) of methyl iodide in 10 ml of absolute tetrahydrofuran.

EXAMPLE 11:

Analogously to Example 6, N-(1-benzyl-2-pyridon-6-yl)-N',N'-di-n-propylformamidine can be manufactured in the form of a viscous oil, R$_f$=0.35 (hexane/ethyl acetate=1:4). There is used as starting material 3 g (14 mmol) of N-(2-hydroxy-6-pyridyl)-N',N'-di-n-propylformamidine and N-(2-pyridon-6-yl)-N',N'-di-n-propylformamidine, 720 mg (15 mmol) of NaH (50% dispersion) and 1.8 ml (15 mmol) of benzyl bromide in 30 ml of absolute tetrahydrofuran.

EXAMPLE 12:

37 ml of a 1.9 molar solution of phosgene in toluene are added dropwise at 0°, while stirring and with the exclusion of moisture, to a solution of 9.1 g (58 mmol) of N,N-di-n-propylpropionamide in 90 ml of absolute chloroform. This mixture is stirred for 5 hours at 0° and then concentrated in vacuo. The residue is taken up in 40 ml of absolute chloroform and the whole is added dropwise to a suspension of 6.4 g (58 mmol) of 2-amino-6-hydroxypyridine in 50 ml of absolute chloroform. 20 ml (145 mmol) of triethylamine are then added and the whole is stirred for a further 20 hours at room temperature. The reaction mixture is then diluted with dichloromethane and washed twice with water. The organic phase is dried over MgSO₄ and then concentrated in vacuo. The resulting crude product is purified chromatographically on silica gel and then crystallised from ether/petroleum ether. N-(2-pyridon-6-yl)-N',N'-di-n-propylpropionamidine and N-(2-hydroxy-6-pyridyl)-N',N'-di-n-propylpropionamidine having a melting point of 112°–113° are obtained.

EXAMPLE 13:

Analogously to Example 12, N-(2-pyridon-6-yl)-N'-ethyl-N'-isopropylacetamidine and N-(2-hydroxy-6-pyridyl)-N'-ethyl-N'-isopropylacetamidine having a melting point of 110°–111° can be manufactured; starting from 8.4 g (65 mmol) of N-ethyl-N-isopropylacetamide, 40 ml of a 1.9 molar solution of phosgene in toluene, 7.2 g (65 mmol) of 2-amino-6-hydroxypyridine and 16.5 g (163 mmol) of triethylamine.

The starting material can be manufactured as follows:

8.7 g (100 mmol) of N-ethyl-N-isopropylamine are mixed carefully with 50 ml of acetic anhydride and heated under reflux for 1 hour. The mixture is then concentrated under a water-jet vacuum. The residue is taken up with dichloromethane and washed once in each case with 2N hydrochloric acid, 2N sodium hydroxide solution and water. The organic phase is dried and concentrated The oil that remains is distilled under a high vacuum N-ethyl-N-isopropylacetamide having a boiling point of 60°–62°/0.08 mm Hg is obtained.

EXAMPLE 14:

2.3 g (14 mmol) of N-(2-hydroxy-6-pyridyl)-N'-cyanoformamidine are added in portions at room temperature over a period of 20 minutes to a stirred solution of 8.3 ml (99 mmol) of n-propylamine in 8 ml of water The reaction mixture is stirred for 2 hours at room temperature It is then extracted three times with chloroform The combined organic phases are dried over MgSO₄ and concentrated by evaporation. The resulting crude product is chromatographed on silica gel with methylene chloride and then crystallised from ether/n-hexane. N-(2-pyridon-6-yl)-N'-propylformamidine and N-(2-hydroxy-6-pyridyl)-N'-propylformamidine having a melting point of 178°–179° are obtained.

The starting material can be manufactured as follows:

11 g (100 mmol) of 2-amino-6-hydroxypyridine and 9.8 g (100 mmol) of ethyl-N-cyanoformamidine are stirred in 100 ml of ethanol for 12 hours under reflux. The reaction mixture is then concentrated in vacuo and purified chromatographically on silica gel. The product so purified is dissolved in chloroform/methanol and crystallised out by adding ether N-(2-hydroxy-6-pyridyl)-N'-cyanoformamidine and N-(2-pyridon-6-yl)-N'-cyanoformamidine having a melting point of 216°–218° are obtained.

EXAMPLE 15:

In a manner analogous to that described in Example 14, N-(2-hydroxy-6-pyridyl)-N',N'-di-n-propylformamidine and N-(2-pyridon-6-yl)-N',N'-di-n-propylformamidine having a melting point of 102°–104° can be manufactured; starting from 13.7 ml (100 mmol) of di-n-propylamine and 2.3 g (14 mmol) of N-(2-hydroxy-6-pyridyl)-N'-cyanoformamidine in 10 ml of water.

EXAMPLE 16:

Analogously to Example 12, N-(2-hydroxy-6-pyridyl)-N',N'-di-n-propylformamidine and N-(2-pyridon-6-yl)-N',N'-di-n-propylformamidine having a melting point of 102°–104° can be obtained; starting from 6.5 g (50 mmol) of N,N-di-n-propylformamide, 35 ml of a 1.9 molar solution of phosgene in toluene, 5.5 g (50 mmol) of 2-amino-6-hydroxypyridine and 12.7 g (125 mmol) of triethylamine.

EXAMPLE 17:

4.25 g (50 mmol) of N-cyanoacetamidine and 6.9 g (50.mmol) of N,N-dipropylamine hydrochloride are heated for 3 hours at 100°, while stirring, in 40 ml of water. The cooled reaction mixture is rendered alkaline with 2N sodium hydroxide solution, whereupon an oil precipitates This oil is separated off and the aqueous phase is extracted once again with dichloromethane. The organic phases are combined and concentrated. The residue is taken up in dioxan and added to a suspension of 4.9 g (44 mmol) of 2-amino-6-hydroxypyridine in 20 ml of xylene and heated for 12 hours under reflux The reaction mixture is concentrated and purified chromatographically on silica gel. The product so purified is crystallised from chloroform/ether. N-(2-hydroxy-6-pyridyl)-N',N'-di-n-propylacetamidine and N-(2-pyridon-6-yl)-N',N'-di-n-propylacetamidine having a melting point of 140°–141° are obtained.

EXAMPLE 18:

3.3 g (20 mmol) of N-(2-hydroxy-6-pyridyl)-N',N'-dimethylformamidine and N-(2-pyridon-6-yl)-N',N'-dimethylformamidine, and 5.1 g (50 mmol) of N,N-di-n-propylamine are stirred for 12 hours under reflux in 20 ml of xylene. The reaction mixture is concentrated by evaporation and then filtered over 10 times the amount of Florisil using dichloromethane. The product-containing fractions are combined and concentrated by evaporation Crystallisation from dichloromethane/n-hexane yields N-(2-hydroxy-6-pyridyl)-N',N'-di-n-propylformamidine and N-(2-pyridon-6-yl)-N',N'-di-n-propylformamidine having a melting point of 102°–104°.

EXAMPLE 19:

1.8 g (10 mmol) of N-(2-pyridon-6-yl)-N'-propylformamidine and N-(2-hydroxy-6-pyridyl)-N'-propylformamidine, 1.9 g (11 mmol) of propyl iodide and 1.5 g (11.mmol) of potassium carbonate are stirred at 80° for 24 hours in 30 ml of absolute ethanol. The reaction mixture is then filtered and concentrated by evaporation The residue is taken up in methylene chloride, washed with water and then dried over Na₂SO₄ and concentrated by evaporation. The resulting crude product is purified chromatographically. Crystallisation from methylene chloride/ether yields N-(2-pyridon-6-yl)-N',N'-di-n-propylformamidine and N-(2-hydroxy-6-pyridyl)-N',N'-di-n-propylformamidine having a melting point of 102°–104°.

EXAMPLE 20:

In a manner analogous to that described in Example 14, N-(2-hydroxy-6-pyridyl)-formamidine and N-(2-pyridon 6-yl)-formamidine can be manufactured; starting from 1.8 g (10 mmol) of N-(2-hydroxy-6-pyridyl)-

N'-cyanoformamidine and 40 ml of ammonia-saturated ethanol at 60°.

EXAMPLE 21:

In a manner analogous to that described in any one of Examples 1 to 20, it is possible to manufacture:
N-(2-hydroxy-3-methyl-6-pyridyl)-N',N'-di-n-propyl-formamidine and N-(3-methyl-2-pyridon-6-yl)-N',N'-di-n-propylformamidine,
N-(5-trifluoromethyl-2-hydroxy-6-pyridyl)-N',N'-di-n-propylformamidine and N-(5-trifluoromethyl-2-pyridon-6-yl)-N',N'-di-n-propylformamidine,
N-(4-chloro-2-hydroxy-6-pyridyl)-N',N'-di-n-propylformamidine and N-(4-chloro-2-pyridon-6-yl)-N',N'-di-n-propylformamidine.

EXAMPLE 22:

In a manner analogous to that described in Example 18, it is possible to manufacture N-(2-hydroxy-6-pyridyl)-N',N'-di-benzyl-formamidine and N-(2-pyridon-6-yl)-N',N'-di-benzyl-formamidine; starting from 3.3 g (20 mmol) of N-(2-pyridon-6-yl)-N',N'-dimethyl-formamidine and 7.9 g (40 mmol) of dibenzylamine.

EXAMPLE 23:

In a manner analogous to that described in Example 14, it is possible to manufacture N-(2-hydroxy-6-pyridyl)-N',N'-di-(2-naphthyl-ethyl)-formamidine and N-(2-pyridon-6-yl)-N',N'-di-(2-naphthylethyl)-formamidine; starting from 6.84 g (40 mmol) of 2-naphthylethylamine and 3.24 g (20 mmol) of N-(2-pyridon-6-yl)-N'-cyanoformamidine in 30 ml of aqueous dioxane (60%).

EXAMPLE 24:

Tablets, each containing 50 mg of the active ingredient, for example N-(2-hydroxy-6-pyridyl)-N',N'-di-n-propylformamidine methanesulphonate and N-(2-pyridon-6-yl)-N',N'-di-n-propylformamidine methanesulphonate, can be manufactured as follows:

| Composition (10,000 tablets) | |
|---|---|
| active ingredient | 500.0 g |
| lactose | 500.0 g |
| potato starch | 352.0 g |
| gelatine | 8.0 g |
| talc | 60.0 g |
| magnesium stearate | 10.0 g |
| silica (highly disperse) | 20.0 g |
| ethanol | q.s. |

The active ingredient is mixed with the lactose and 292 g of the potato starch, the mixture is moistened with an alcoholic solution of the gelatine and granulated through a sieve. After drying, the remainder of the potato starch, the talc, the magnesium stearate and the highly disperse silica are mixed in and the mixture is compressed to form tablets that each weigh 145.0 mg and contain 50.0 mg of active ingredient and that can, if desired, be provided with dividing notches for finer adjustment of the dosage.

EXAMPLE 25:

Lacquer-coated tablets, each containing 100 mg of the active ingredient, for example N-(2-hydroxy-6-pyridyl)-N',N'-di-n-propylformamidine methanesulphonate and N-(2-pyridon-6-yl)-N',N'-di-n-propylfor-mamidine methanesulphonate, can be manufactured as follows:

| Composition (for 1000 tablets) | |
|---|---|
| active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste, produced from 15 g of the corn starch and water (while heating), and granulated. The granulate is dried and the remainder of the corn starch, the talc and the calcium stearate are added and mixed with the granulate. The mixture is compressed to form tablets (weight: 280 mg) and the tablets are coated with a solution of the hydroxypropylmethylcellulose and the shellac in methylene chloride; final weight of the lacquer-coated tablet: 283 mg.

EXAMPLE 26:

In a manner analogous to that described in Examples 24 and 25, it is also possible to manufacture tablets or lacquer-coated tablets containing a compound according to the invention, for example, according to Examples 1 to 23.

We claim:

1. A pyridine derivative of the formula

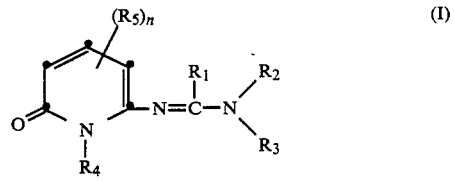

wherein $R_1$ is hydrogen of $C_{1-7}$ alkyl; one of $R_2$ and $R_3$ is hydrogen, $C_{1-7}$ alkyl, or aryl-$C_{1-7}$ alkyl in which aryl is selected from phenyl, naphthyl, indenyl, pentalenyl, azulenyl and pyridyl; and the other is $C_{1-7}$ alkyl or an aryl-$C_{1-7}$ alkyl in which aryl is selected from phenyl, naphthyl, indenyl, pentalenyl, azulenyl and pyridyl;, $R_4$ is hydrogen; and $R_5$ represents $C_1$-$C_7$-alkyl, halogen, $C_1$-$C_7$-alkoxy, $C_1$-$C_7$-alkylthio $C_1$-$C_7$-alkanesulphinyl, $C_1$-$C_7$-alkanesulphonyl, carboxy, $C_2$-$C_8$-alkoxycarbonyl, carbamoyl, $C_1$-$C_7$-alkylcarbamoyl, di-$C_1$-$C_7$-alkylcarbamoyl, cyano or trifluoromethyl, and the index n represents 0, 1 or 2; and wherein each aryl is unsubstituted or polysubstituted by the same or different substituents selected form halogen, $C_{1-7}$ alkyl, $C_{1-7}$ alkoxy, hydroxy, and $C_{2-8}$ alkanoyloxy; or a tautomer thereof or a pharmaceutically acceptable salt of said compound of tautomer.

2. The compound, tautomer or salt of claim 1 wherein $R_1$ is hydrogen or $C_{1-4}$ alkyl; $R_2$ is $C_{1-4}$ alkyl; and $R_3$ is $C_{1-4}$ alkyl or phenyl-$C_{1-4}$ alkyl.

3. The compound, tautomer or salt of claim 2 wherein $R_1$ is hydrogen or methyl; $R_2$ and $R_3$ are each propyl; or $R_2$ is methyl and $R_3$ is 2-phenethyl.

4. The compound, tautomer or salt of claim 1 wherein $R_1$ is hydrogen; $R_2$ is $C_{1-4}$ alkyl; $R_3$ is $C_{1-4}$ alkyl; and $R_4$ is hydrogen.

5. The compound, tautomer or salt of claim 4 wherein $R_2$ and $R_3$ are each propyl.

6. The compound, tautomer or salt of claim 1 wherein $R_1$ is methyl; $R_2$ is $C_{1-4}$ alkyl; and $R_3$ is $C_{1-4}$ alkyl.

7. The compound, tautomer or salt of claim 6 wherein $R_2$ and $R_3$ are each propyl.

8. A compound according to claim 1 being N-(2-hydroxy-6-pyridyl)-N',N'-di-n-propylformamidine and N-(2-pyridon-6-yl)-N',N'-di-n-propylformamidine or a salt thereof.

9. A compound according to claim 1 being N-(2-hydroxy-6-pyridyl)-N',N'-di-n-propylacetamidine and N-(2-pyridon-6-yl)-N',N'-di-n-proylacetamidine or a salt thereof.

10. A compound according to claim 1 being N-(2-hydroxy-6-pyridyl)-N',N'-dimethylformamidine and N-(2-pyridon-6-yl)-N',N'-dimethylformamidine or a pharmaceutically acceptable salt thereof.

11. A compound according to claim 1 being N-(2-hydroxy-6-pyridyl)-N',-methyl-N'-butylformamidine and N-(2-pyridon-6-yl)-N'-methyl-N'-butylformamidine or a pharmaceutically acceptable salt thereof.

12. A compound according to claim 1 being N-(2-hydroxy-6-pyridyl)-N'-methyl-N'-(2-phenylethyl)-acetamidine and N-(2-pyridon-6-yl)-N',-methyl-N'-(2-phenylethyl-acetamidine or pharmaceutically acceptable salt thereof.

13. A compound according to claim 1 being N-(2-pyridon-6-yl)-N'-ethyl-N'-isopropylacetamidine and N-(2-hydroxy-6-pyridyl)-N'-ethyl-N'isopropylacetamidine or a pharmaceutically acceptable salt thereof.

14. A compound according to claim 1 being N-(2-pyridon-6-yl)-N'-ethyl-N'-isopropylformamidine and N-(2-hydroxy-6-pyridyl)-N'-ethyl-N'-isopropylformamidine or a pharamaceutically acceptable salt thereof.

15. A compound according to claim 1 being N-(2-pyridon-6-yl)-N'-propylformamidine and N-(2-hydroxy-6-pyridyl)-N'-propylformamidine or a pharmaceutically acceptable salt thereof.

16. A compound according to claim 1 being N-(2-pyridon-6-yl)-N',N'-dipropylpropionamidine and N-(2-hydroxy-6-pyridyl)-N',N'-dipropylpropionamidine or a pharmaceutically acceptable salt thereof.

17. A compound according to claim 1 being N-(2-pyridon-6-yl)-N',-propylacetamidine and N-(2-hydroxy-6-pyridyl)-N'-propylacetamidine or a pharmaceutically acceptable salt thereof.

18. A compound according to claim 1 being N-(2-hydroxy-6-pyridyl)-N',N'-di-(2-naphthylethyl)-formamidine and N-(2-pyridon-6-yl)-N',N'-di-(2napphthylethyl)-formamidine or a pharmaceutically acceptable salt thereof.

19. A compound according to claim 1 being N-(2-hydroxy-6-pyridyl)-N',N'-di-benzyl-formamidine and N-(2-pyridon-6-yl)-N',N'-di-benzyl-formamidine or a pharmaceutically acceptable salt thereof.

20. A catecholamine-O-methyltransferase inhibiting pharmaceutical composition comprising a catecholamine-O-methyltransferase inhibiting effective amount of a compound, tautomer or salt of claim 1 and a pharmaceutically acceptable adjunct.

21. A method of inhibiting catecholamine-O-methyltransferase in an animal in need thereof comprising administering to said animal a catecholamine-O-methyltransferase inhibiting effective amount of a compound, tautomer of salt of claim 1.

22. A method of treating depression in an animal in need thereof comprising administering to said animal an antidepressant effective amount of a compound, tautomer of salt of claim 1.

23. A method of treating Parkinson's disease in an animal in need thereof comprising administering to an animal in need thereof an anti-Parkinson's disease effective amount of a compound, tautomer or salt of claim 1.

24. A method of treating a nootropically responsive condition in an animal in need thereof comprising administering to said animal a nootropically effective amount of a compound, tautomer or salt of claim 1.

25. The method of claim 21 wherein said animal is a human.

* * * * *